United States Patent
Yamashita et al.

(10) Patent No.: US 12,354,047 B2
(45) Date of Patent: Jul. 8, 2025

(54) ESTIMATION DEVICE, ESTIMATION METHOD, AND ESTIMATION PROGRAM

(71) Applicant: Nippon Telegraph and Telephone Corporation, Tokyo (JP)

(72) Inventors: Jumpei Yamashita, Musashino (JP); Akira Kataoka, Musashino (JP); Hidetaka Koya, Musashino (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 125 days.

(21) Appl. No.: 18/279,179

(22) PCT Filed: Mar. 5, 2021

(86) PCT No.: PCT/JP2021/008837
§ 371 (c)(1),
(2) Date: Aug. 28, 2023

(87) PCT Pub. No.: WO2022/185550
PCT Pub. Date: Sep. 9, 2022

(65) Prior Publication Data
US 2024/0135300 A1    Apr. 25, 2024

(51) Int. Cl.
G06Q 10/0639    (2023.01)
G06T 7/254    (2017.01)
G06T 7/62    (2017.01)

(52) U.S. Cl.
CPC ....... *G06Q 10/06398* (2013.01); *G06T 7/254* (2017.01); *G06T 7/62* (2017.01); *G06T 2207/30201* (2013.01)

(58) Field of Classification Search
CPC ..... G06Q 10/06398; G06T 7/254; G06T 7/62; G06T 2207/30201; G05B 19/418;
(Continued)

(56) References Cited

U.S. PATENT DOCUMENTS 6,097,295 A * 8/2000 Griesinger ............... A61B 5/18
340/576
6,346,887 B1 * 2/2002 Van Orden ............ A61B 5/163
340/576
(Continued)

FOREIGN PATENT DOCUMENTS

JP    2007099249 A  *  4/2007
JP    2016151849 A  *  8/2016

OTHER PUBLICATIONS

Bergamin et al., "Latency of the Pupil Light Reflex: Sample Rate, Stimulus Intensity, and Variation in Normal Subjects," Investigative Ophthalmology & Visual Science, Apr. 2003, 44(4):1546-1554.
(Continued)

*Primary Examiner* — Adnan Aziz
(74) *Attorney, Agent, or Firm* — Fish & Richardson P.C.

(57) ABSTRACT

An estimation device includes processing circuitry configured to acquire time-series data of a pupil diameter during work of a subject of work performance estimation, smooth the time-series data of the pupil diameter of the subject by a first time window, smooth the time-series data of the pupil diameter by a second time window that is a time window larger than the first time window, calculate a difference between time-series data of the pupil diameter smoothed by the first time window and time-series data of the pupil diameter smoothed by the second time window, and estimate a level of work performance of the subject based on a magnitude of the difference between the time-series data of the pupil diameter smoothed by the first time window and the time-series data of the pupil diameter smoothed by the second time window, and output a result of the estimation.

9 Claims, 5 Drawing Sheets

(58) Field of Classification Search
CPC ..... G08B 21/06; G02B 27/0093; A61B 3/112; A61B 3/11; A61B 3/113; A61B 5/00; A61B 5/11; A61B 5/16; A61B 5/18; A61B 5/163
See application file for complete search history.

(56) References Cited

U.S. PATENT DOCUMENTS

| | | | | |
|---|---|---|---|---|
| 2017/0293356 A1* | 10/2017 | Khaderi | | A61B 3/113 |
| 2019/0175090 A1* | 6/2019 | Reiner | | A61B 5/165 |
| 2020/0187840 A1* | 6/2020 | Yamaji | | G08G 1/16 |
| 2021/0264129 A1* | 8/2021 | Yamagishi | | A61B 3/112 |
| 2021/0282639 A1* | 9/2021 | Yokoyama | | G02B 27/02 |

OTHER PUBLICATIONS

Oken et al., "Vigilance, alertness, or sustained attention: physiological basis and measurement," Clin. Neurophysiol., Sep. 2006, 117(9):1885-1901.

Wilhelm et al., "Pupillographic Assessment of Sleepiness in Sleep-deprived Healthy Subjects," Sleep, May 1998, 21(3):258-265.

* cited by examiner

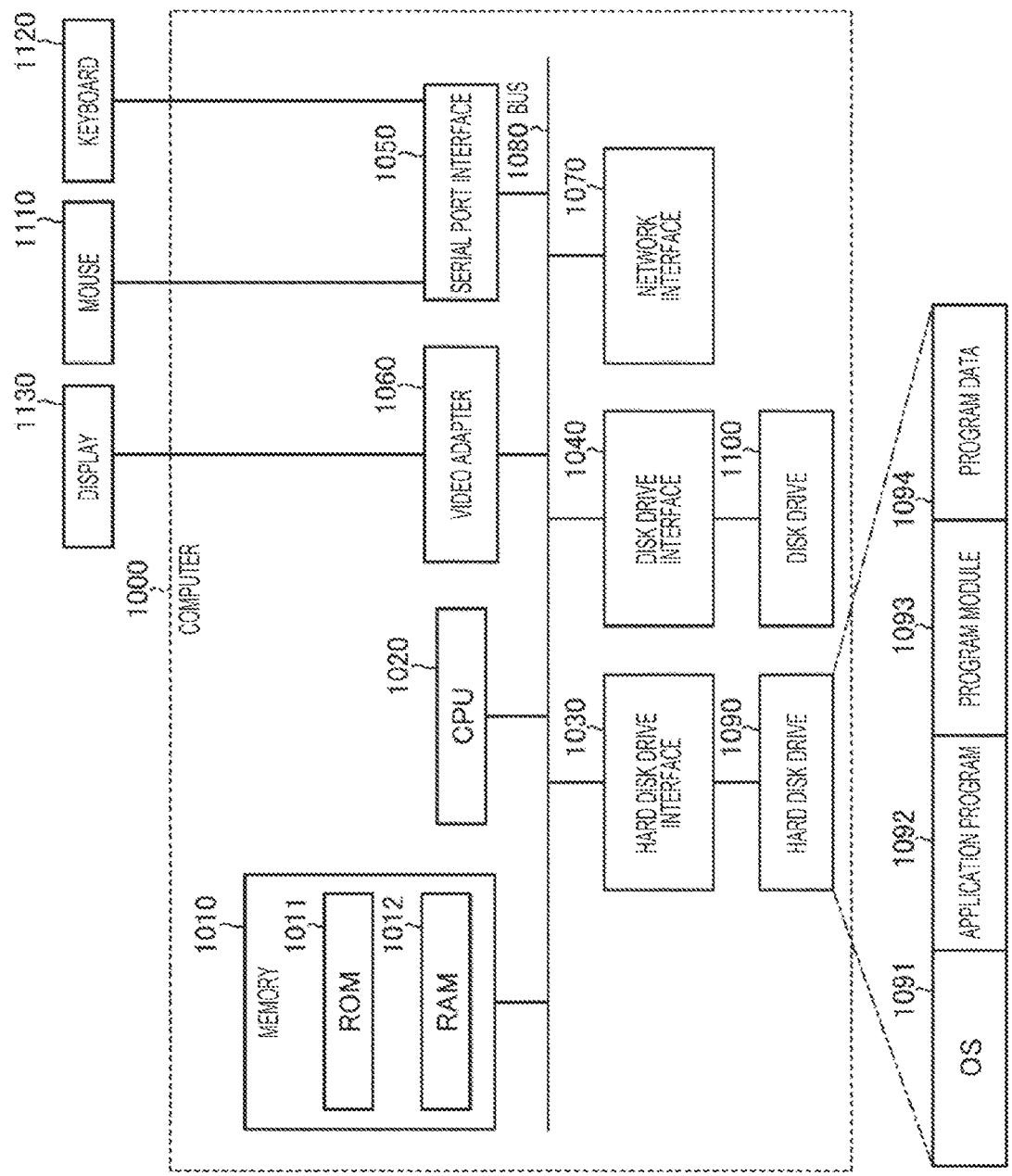

ESTIMATION DEVICE, ESTIMATION METHOD, AND ESTIMATION PROGRAM

CROSS-REFERENCE TO RELATED APPLICATIONS

This application is a National Stage application under 35 U.S.C. § 371 of International Application No. PCT/JP2021/008837, having an International Filing Date of Mar. 5, 2021. The disclosure of the prior application is considered part of the disclosure of this application, and is incorporated by reference in its entirety into this application.

TECHNICAL FIELD

The present invention relates to an estimation device, an estimation method, and an estimation program.

BACKGROUND ART

When a human performs work (performs a cognitive task) while the human is visually checking something, a performance of the human performing the task is sometimes good and sometimes bad. Here, as a method of estimating a performance of a worker performing a task, there is a method of using a variation amount of a pupil diameter of the worker.

When a performance of a worker performing a task (hereinafter, appropriately referred to as a "task performance") is estimated by the method using a variation amount of a pupil diameter of the worker, the worker is placed in darkness for a predetermined time, and the variation amount of the pupil diameter of the worker is measured.

Here, it is known that a large wave appears in the variation amount of the pupil diameter of the worker in a case where the task performance of the worker is deteriorated such as when the worker is hindered from sleeping for a long time, for example (see Non Patent Literatures 1 and 2).

Therefore, it is estimated that the task performance of the worker is low in a case where the variation amount of the pupil diameter of the worker in darkness is large, and the task performance of the worker is high in a case where the variation amount of the pupil diameter is small.

The reason why the worker is placed in darkness for the predetermined time when the task performance of the worker is estimated is that, it is known that when the brightness of the place at which the worker is gazing changes, a temporary variation occurs in the pupil diameter due to light adaptation or dark adaptation, and the influence of a temporary variation is to be removed.

CITATION LIST

Non Patent Literature

Non Patent Literature 1: Pupillographic Assessment of Sleepiness in Sleep-deprived Healthy Subjects. Sleep, 21, 258-265., [Retrieved on Feb. 19, 2021], Internet <URL: pubmed.ncbi.nlm.nih.gov/9595604/>
Non Patent Literature 2: B.S. Oken, M.C. Salinsky, and S.M. Elsas, Vigilance, alertness, or sustained attention: physiological basis and measurement, Clin Neurophysiol. (2006) September; 117 (9): 1885-1901
Non Patent Literature 3: Oliver Bergamin, Randy H. Kardon, Latency of the Pupil Light Reflex: Sample Rate, Stimulus Intensity, and Variation in Normal Subjects, Investigative Ophthalmology & Visual Science April 2003, Vol. 44, 1546-1554. [Retrieved on Feb. 19, 2021], Internet <URL:iovs.arvojournals.org/article.aspx?articleid=2123928>

SUMMARY OF INVENTION

Technical Problem

However, in a related art, in order to accurately acquire the brightness of the place gazed by the worker during the work, a line-of-sight position measuring device of the worker and a device for measuring the brightness of the place gazed by the worker are necessary. For this reason, there is a problem that the cost for estimating the task performance of the worker increases and it is not convenient.

Therefore, an object of the present invention is to solve the problem and to facilitate estimation of a task performance of a worker.

Solution to Problem

In order to solve the above problem, an estimation device according to the present invention includes: processing circuitry configured to: acquire time-series data of a pupil diameter during work of a subject of work performance estimation; smooth the time-series data of the pupil diameter of the subject by a first time window; smooth the time-series data of the pupil diameter by a second time window that is a time window larger than the first time window; calculate a difference between time-series data of the pupil diameter smoothed by the first time window and time-series data of the pupil diameter smoothed by the second time window; and estimate a level of work performance of the subject on the basis of a magnitude of the difference between the time-series data of the pupil diameter smoothed by the first time window and the time-series data of the pupil diameter smoothed by the second time window, and output a result of the estimation.

Advantageous Effects of Invention

According to the present invention, estimation of task performance of a worker can be facilitated.

BRIEF DESCRIPTION OF DRAWINGS

FIG. 5 is a diagram illustrating a configuration example of a computer that executes an estimation program.

DESCRIPTION OF EMBODIMENTS

Hereinafter, modes (embodiments) for carrying out the present invention will be described separately into a first embodiment and a second embodiment with reference to the drawings. The present invention is not limited to the embodiments described below.

[Overview of Each Embodiment] First, an operation outline of an estimation device of each embodiment will be described. The estimation device estimates a work performance (task performance) of a worker executing a task.

First, the estimation device estimates the task performance of a worker (a subject for estimation of the task performance) on the basis of time-series data of a pupil diameter of the subject executing a task. Here, the pupil diameter of the subject changes depending on a change in brightness of a place gazed by the subject.

However, the variation of the pupil diameter depending on the change in brightness of the place gazed by the subject occurs in a relatively long time scale. For example, it is known that the variation of the pupil diameter depending on the change in brightness of the place gazed by the subject occurs over 100 ms or more (see Non Patent Literature 3). That is, the variation of the pupil diameter depending on the change in brightness of the place gazed by the subject can be considered as a macro variation.

Therefore, the estimation device obtains a variation (hereinafter, referred to as micro variation as appropriate) obtained by removing the macro variation from the time-series data of the pupil diameter of the subject. Then, the estimation device estimates the level of the task performance of the subject on the basis of the micro variation of the time-series data of the pupil diameter of the subject.

Figure 1:
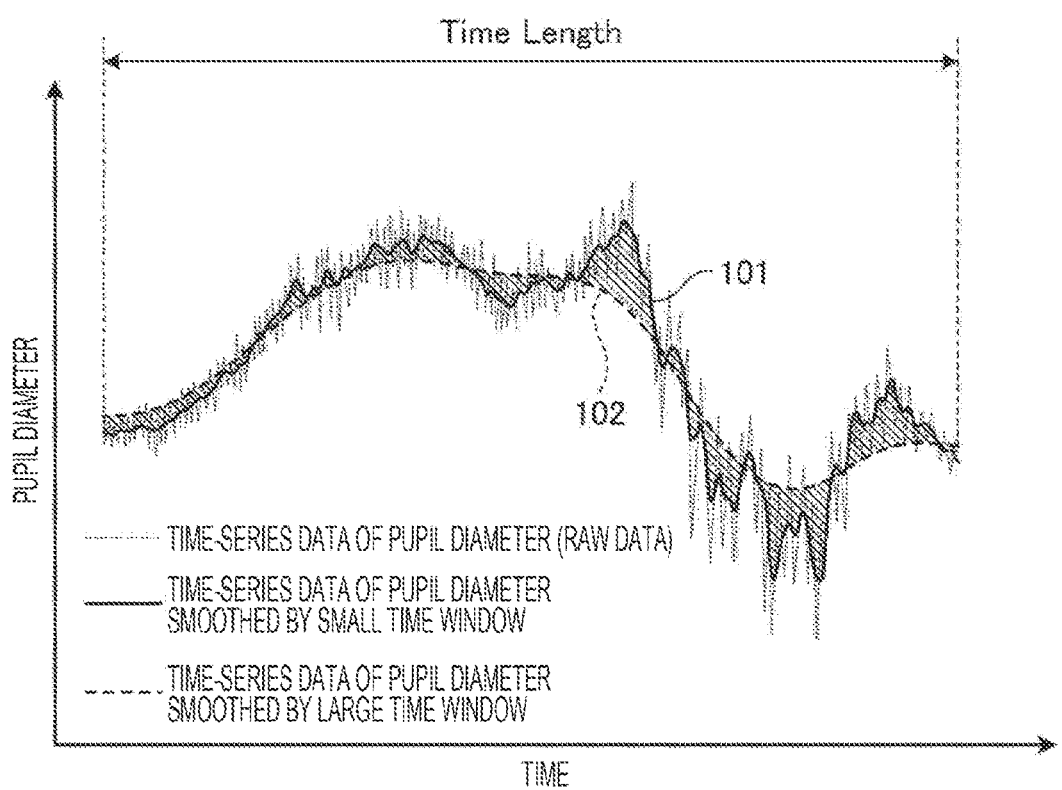
FIG. 1 is a diagram for explaining a macro variation and a micro variation in each embodiment.

FIG. 1 is a diagram for explaining a micro variation in time-series data of a pupil diameter of a subject. For example, as illustrated in FIG. 1, the estimation device calculates data obtained by smoothing the time-series data of the pupil diameter of the subject with a small time window and data obtained by smoothing the time-series data of the pupil diameter with a large time window (macro variation). Next, the estimation device sets the average value of the differences between these pieces of data as the micro variation of the time-series data of the pupil diameter. Then, the estimation device estimates the level of the task performance of the subject on the basis of the micro variation of the time-series data of the pupil diameter.

For example, the estimation device estimates that the task performance of the subject is lower as the micro variation of the time-series data of the pupil diameter of the subject is larger, and estimates that the task performance of the subject is higher as the micro variation is smaller.

That is, the estimation device separates the micro pupil diameter variation correlated with the task performance from the temporary macro pupil diameter variation due to the light amount change at the position (gaze target) at which the subject is gazing, and estimates the level of the task performance. As a result, the estimation device can estimate the level of the task performance of the subject without measuring the brightness of the position at which the subject is gazing.

First Embodiment

[Configuration Example] Next, a configuration example of an estimation device 10 of a first embodiment will be described with reference to FIG. 2. The estimation device 10 includes an input/output unit 11, a storage unit 12, and a control unit 13.

The input/output unit 11 manages input and output of various types of data, and receives input of, for example, time-series data of a pupil diameter of a subject performing a task, who is a person whose task performance is to be estimated. Note that the pupil diameter of the subject is acquired by, for example, an optical device using an infrared camera or a visible light camera.

In addition, the input/output unit 11 outputs a level of the task performance of the subject estimated by the control unit 13. The storage unit 12 stores various types of data to be referred to when the control unit 13 executes processing.

The control unit 13 controls the entire estimation device 10. The control unit 13 includes, for example, a data acquisition unit (acquisition unit) 131, a first smoothing processing unit 132, a second smoothing processing unit 133, a calculation unit 134, and an estimation unit 135.

The data acquisition unit 131 acquires the time-series data of the pupil diameter during work of the subject via the input/output unit 11. For example, the data acquisition unit 131 acquires the time-series data of the pupil diameter during the work of the subject by an optical device connected to the estimation device 10. The data acquisition unit 131 outputs the acquired time-series data of the pupil diameter to the first smoothing processing unit 132 and the second smoothing processing unit 133.

The first smoothing processing unit 132 smooths the time-series data of the pupil diameter output from the data acquisition unit 131 using a first time window (small time window). The second smoothing processing unit 133 smooths the time-series data of the pupil diameter by a second time window (large time window). The first time window is a time window smaller than the second time window. The first time window is, for example, a time window having a length of 50 ms. The second time window is, for example, a time window having a length of 100 ms.

For example, the first smoothing processing unit 132 smooths the time-series data of the pupil diameter illustrated in FIG. 1 with a small time window to create the time-series data indicated by the reference numeral 101. Furthermore, the second smoothing processing unit 133 smooths the time-series data of the pupil diameter illustrated in FIG. 1 with a large time window to create the time-series data indicated by the reference numeral 102.

Figure 2:
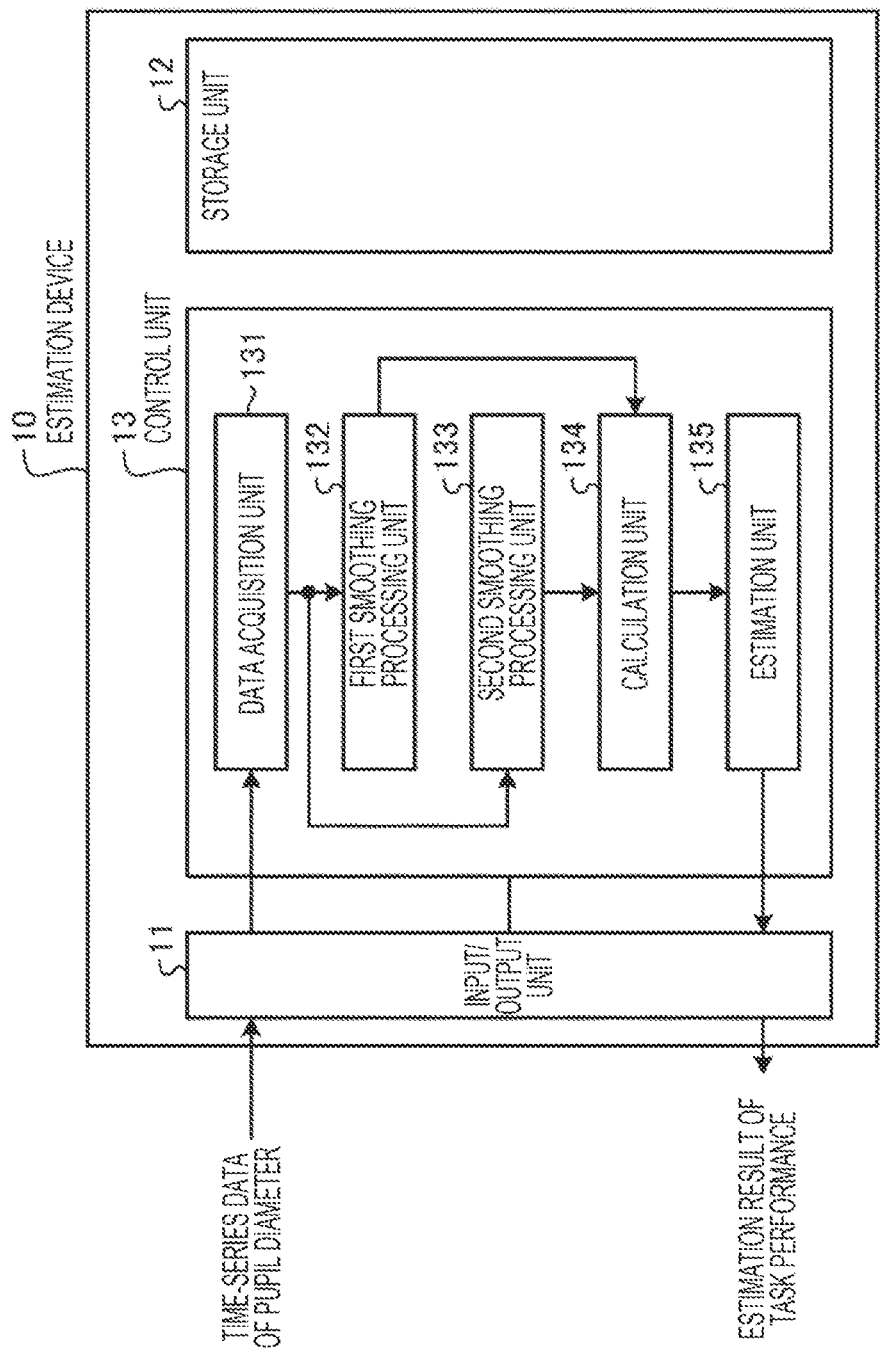
FIG. 2 is a diagram illustrating a configuration example of an estimation device according to each embodiment.

The description returns to FIG. 2. The calculation unit 134 calculates a difference between the time-series data of the pupil diameter smoothed by the first smoothing processing unit 132 and the time-series data of the pupil diameter smoothed by the second smoothing processing unit 133.

For example, the calculation unit 134 calculates an absolute value of a value obtained by first differentiating the time-series data of the pupil diameter smoothed by the first smoothing processing unit 132, and calculates an average value of the calculated absolute values. For example, the calculation unit 134 calculates a value obtained by adding up absolute values of values obtained by first differentiating the time-series data of the pupil diameter smoothed by the first smoothing processing unit 132 and then dividing the sum by a time length of the time-series data of the pupil diameter. For example, the calculation unit 134 calculates the above value (variation amount of the pupil diameter in a small time window) on the basis of the following Equation (1).

[Math. 1]

Time Length: LENGTH OF TIME SECTION IN WHICH VARIATION AMOUNT OF PUPIL DIAMETER IN SMALL TIME WINDOW IS CALCULATED        EQUATION (1)

$n$: TIME

Micro_pupil_size$_n$: VALUE OF PUPIL DIAMETER SMOOTHED BY SMALL TIME WINDOW AT TIME $n$ VARIATION AMOUNT OF PUPIL DIAMETER IN SMALL TIME WINDOW =

$$\sum_{n=1}^{Time\_Length-1} \frac{|Micro\_pupil\_size_{n+1} - Micro\_pupil\_size_n|}{(Time\_Length - 1)}$$

For example, the calculation unit 134 similarly calculates an absolute value of a value obtained by first differentiating the time-series data of the pupil diameter smoothed by the second smoothing processing unit 133, and calculates an average value of the calculated absolute values. For example, the calculation unit 134 calculates a value obtained by adding up values obtained by first differentiating the time-series data of the pupil diameter smoothed by the second smoothing processing unit 133 and then dividing the sum by a time length of the time-series data of the pupil diameter. For example, the calculation unit 134 calculates the above value (variation amount of the pupil diameter of the macro) on the basis of the following Equation (2).

[Math. 2]

Time Length: LENGTH OF TIME SECTION IN WHICH MACRO VARIATION AMOUNT OF PUPIL DIAMETER IS CALCULATED        EQUATION (2)

$n$: TIME

Macro_pupil_size$_n$: VALUE OF PUPIL DIAMETER SMOOTHED BY LARGE TIME WINDOW AT TIME $n$ MACRO VARIATION AMOUNT OF PUPIL DIAMETER =

$$\sum_{n=1}^{Time\_Length-1} \frac{|Macro\_pupil\_size_{n+1} - Macro\_pupil\_size_n|}{(Time\_Length - 1)}$$

Then, the calculation unit 134 calculates a difference (micro variation amount of the pupil diameter) between the calculated pupil diameter variation amount and the variation amount of the pupil diameter of the macro in the small time window.

The micro variation amount of the pupil diameter calculated as described above generally becomes a larger value as a difference between a length of data smoothed in a small time window (for example, see the reference numeral 101 in FIG. 1) and a length of data smoothed in a large time window (for example, see the reference numeral 102 in FIG. 1) is larger.

The description returns to FIG. 2. The estimation unit 135 estimates the level of work performance of the subject on the basis of the difference (micro variation amount of the pupil diameter) between the variation amount of the pupil diameter and the variation amount of the pupil diameter of the macro in the small time window calculated by the calculation unit 134.

For example, the estimation unit 135 estimates that the larger the micro variation amount of the pupil diameter, the lower the work performance of the subject. Furthermore, the estimation unit 135 estimates that the smaller the micro variation amount of the pupil diameter, the higher the work performance of the subject. The estimation unit 135 then outputs the result of estimation of the task performance of the subject.

As a result, the estimation device 10 can estimate the level of the task performance of the subject without measuring the brightness of the position (gaze target) at which the subject is gazing.

When outputting the time-series data of the pupil diameter to the first smoothing processing unit 132 and the second smoothing processing unit 133, the data acquisition unit 131 may output, as the valid data, the time-series data of the pupil diameter excluding the occurrence of blinking and the periods before and after the blinking as the invalid sections among the time-series data of the pupil diameter of the subject acquired from the optical device or the like.

Figure 4:
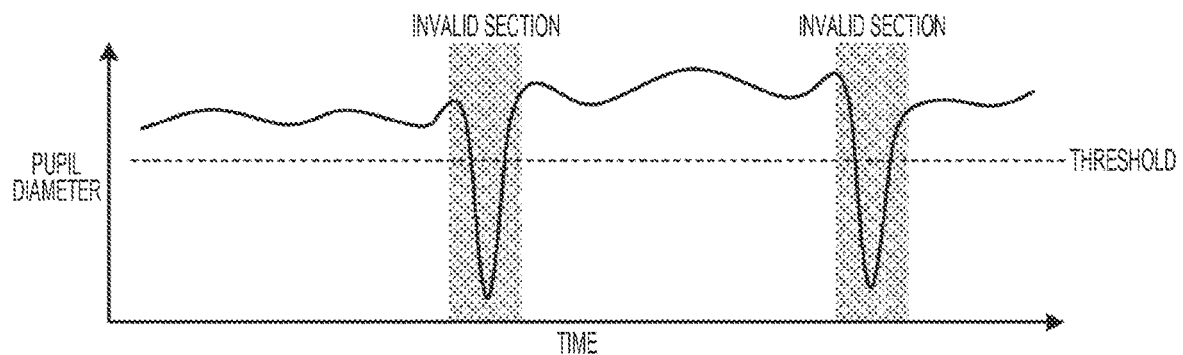
FIG. 4 is a diagram for explaining time-series data of a pupil diameter of a subject and an invalid section in the time-series data.

Here, when the data acquisition unit 131 detects the occurrence of blinking, in consideration of the nature of a biological system that controls the pupil diameter, an algorithm may be used in which a case where such a small pupil diameter that cannot be calculated unless the eyelid is closed is measured (for example, a case where the pupil diameter illustrated in FIG. 4 is equal to or smaller than a predetermined threshold) is regarded as the occurrence of blinking.

For example, consider a case where the time-series data of the pupil diameter of the subject indicates values illustrated an FIG. 4. In this case, as illustrated in FIG. 4, the data acquisition unit 131 sets, as invalid spaces, a section in which the value of the pupil diameter is equal to or smaller than the predetermined threshold and sections before and after the section. The data acquisition unit 131 then outputs the time-series data of the pupil diameter obtained by excluding the data in the invalid spaces from the time-series data of the pupil diameter of the subject.

In this way, the first smoothing processing unit 132 and the second smoothing processing unit 133 can accurately smooth the time-series data of the pupil diameter of the subject. As a result, the calculation unit 134 can accurately calculate the micro variation amount of the pupil diameter of the subject.

Figure 3:
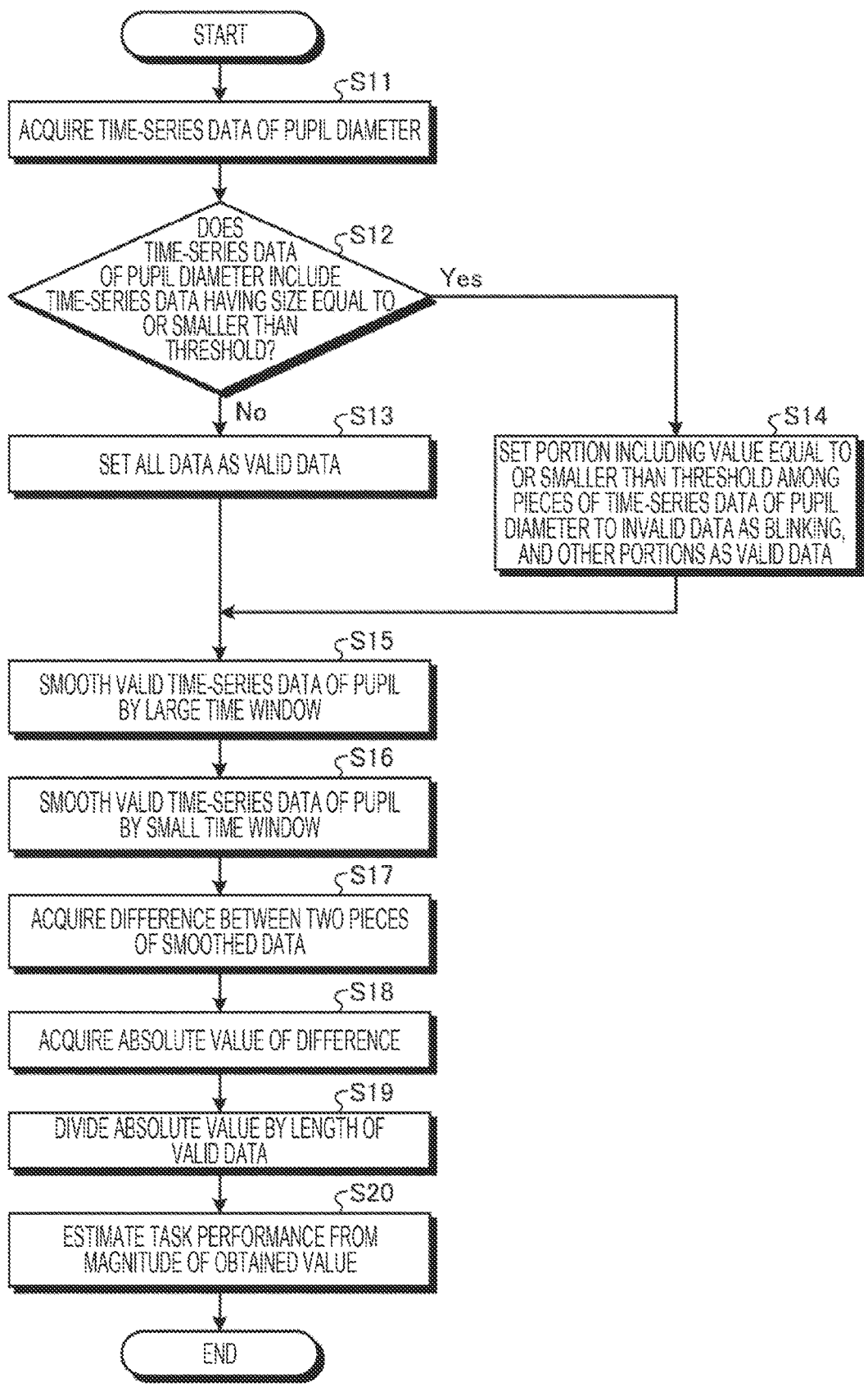
FIG. 3 is a flowchart illustrating an example of a processing procedure of the estimation device of FIG. 2.

[Example of Processing Procedure] Next, an example of a processing procedure of the estimation device 10 be described with reference to FIG. 3. First, the data acquisition unit 131 of the estimation device 10 acquires time-series data of a pupil diameter of a subject (S11).

Here, in a case where the time-series data of the pupil diameter does not include time-series data having a size equal to or smaller than the threshold (No in S12), the data acquisition unit 131 sets all the data acquired in S11 as valid data (S13), and outputs the valid data to the first smoothing processing unit 132 and the second smoothing processing unit 133. The process proceeds to S15.

On the other hand, in a case where the size equal to or smaller than the threshold is included in the time-series data of the pupil diameter (Yes in S12), the data acquisition unit 131 sets a portion including a value equal to or smaller than the threshold in the time-series data of the pupil diameter to invalid data as blinking, and sets the other portion as valid data (S14). The data acquisition unit 131 outputs the valid data to the first smoothing processing unit 132 and the second smoothing processing unit 133, The process proceeds to S15.

The first smoothing processing unit 132 smooths the valid data (valid time-series data of the pupil diameter) output from the data acquisition unit 131 with a large time window (S15). The second smoothing processing unit 133 smooths the valid data (valid time-series data of the pupil diameter) output from the data acquisition unit 131 with a small time window (S16).

Then, the calculation unit 134 acquires a difference between the two pieces of smoothed data (the data smoothed in S15 and the data smoothed in S16) (S17), acquires an absolute value of the difference acquired in S17 (S18), and divides the absolute value acquired in S18 by the length of the valid data (S19). The length of the valid data here is the length of the time section that is not excluded as the blinking period among the time sections targeted for estimation of the task performance of the subject.

After S19, the estimation unit 135 estimates the level of the task performance of the subject from the magnitude of the value obtained in S19 (S20). For example, the estimation unit 135 estimates that the larger the value (that is, the micro variation amount of the pupil diameter of the subject) obtained in S19, the lower the task performance of the subject. The estimation unit 135 then outputs the result of the level of estimation of the task performance of the subject.

As a result, the estimation device 10 can estimate the level of the task performance of the subject without measuring the brightness of the position (gaze target) at which the subject is gazing.

[Second Embodiment] The above-described calculation unit 134 may calculate an average value of absolute values of differences between the time-series data of the pupil diameter smoothed by the small time window and the time-series data of the pupil diameter smoothed by the large time window at each time as the micro variation amount of the pupil diameter. For example, the calculation unit 134 may calculate the micro variation amount of the pupil diameter on the basis of the following Equation (3).

[Math. 3]

Time Length: LENGTH OF TIME SECTION IN WHICH MICRO VARIATION AMOUNT OF PUPIL DIAMETER IS CALCULATED $n$: TIME Micro_pupil_size$_n$: VALUE OF PUPIL DIAMETER SMOOTHED BY SMALL TIME WINDOW AT TIME $n$ Macro_pupil_size$_n$: VALUE OF PUPIL DIAMETER SMOOTHED BY LARGE TIME WINDOW AT TIME $n$

MICRO VARIATION AMOUNT OF PUPIL DIAMETER =

$$\sum_{n=1}^{Time\_Length\ h} \frac{|\text{Micro\_pupil\_size}_n - \text{Macro\_pupil\_size}_n|}{(\text{Time\_Length})}$$

EQUATION (3)

The micro variation amount of the pupil diameter calculated as described above generally increases as the area of a region (for example, hatched portions in FIG. 1) between data smoothed by a small time window (for example, see the reference numeral 101 in FIG. 1) and data smoothed by a large time window (for example, see the reference numeral 102 in FIG. 1) increases.

[Method A and Method B] The estimation device 10 may select whether to use the calculation method (method A) described in the first embodiment or the calculation method (method B) described in the second embodiment for calculating the micro variation amount of the pupil diameter according to the level of the time resolution of the measurement device (for example, an optical device) that measures the pupil diameter of the subject.

For example, in a case where the time resolution in the measurement of the pupil diameter of the measurement device is relatively high, the estimation device 10 uses the method A as a method of calculating the micro variation amount of the pupil diameter. On the other hand, in a case where the time resolution in the measurement of the pupil diameter of the measurement device is relatively low, the estimation device 10 uses the method B as a method of calculating the micro variation amount of the pupil diameter.

The reason will be described below. In general, measurement noise exists in the raw data of the measurement result of the pupil diameter. Here, it is assumed that a small amount of vibration (for example, as compared with the true value, the measured value substantially alternately varies ± for each time point) of the measured value of the pupil diameter is observed for each time point in the raw data of the measured result of the pupil diameter.

As described above, since measurement noise exists in the raw data of the measurement result of the pupil diameter, it is desirable to use time-series data obtained by smoothing the raw data with a time window of a predetermined length. Therefore, when the estimation device 10 calculates the micro variation amount of the pupil diameter, for example, it is desirable to use the time-series data obtained by smoothing the measurement result of the pupil diameter with a time window of about 50 ms.

Here, the time resolution in the measurement of the pupil diameter different for each measurement device. Therefore, for example, there may be a situation in which a measurement device having a high time resolution can perform measurement 1000 times per second, but a measurement device having a low time resolution can perform measurement only 20 times per second.

Here, if the time resolution of the measurement device is high (for example, measurement frequency=1000 Hz or the like), the time-series data of the pupil diameter can be smoothed by a time window of 50 ms (time window of 50 points in length). Therefore, the estimation device 10 can calculate the micro pupil diameter variation amount by the method A by setting the time-series data smoothed by the time window of 50 ms as "data smoothed by a small time window" and setting the time-series data smoothed by a time window equal to or larger than that (for example, 100 ms or the like) as "data smoothed by a large time window".

On the other hand, when the time resolution of the measurement device is low (for example, measurement frequency=20 Hz or the like), the estimation device 10 cannot smooth the time-series data of the pupil diameter with the time window of 50 ms (time window of 50 points in length).

Therefore, the estimation device 10 uses the raw data as "data smoothed by a small time window", and sets the time-series data smoothed in a time window of equal to or larger than that (for example, 100 ms or the like) as "data smoothed by a large time window". Here, in a case where the estimation device 10 uses raw data as "data smoothed by a small time window", the variation amount in "data smoothed by a small time window" is greatly affected by noise and thus lacks reliability. Accordingly, the estimation device 10 preferably applies the method B to the calculation of the micro variation amount of the pupil diameter rather than the method A.

This is because the method B is a method of calculating the difference in area instead or the variation amount of the pupil diameter itself, and is robust against noise even if "data smoothed by a small time window" includes small steps of vibration (for example, the measured value almost alternately varies ± for each time point as compared with the true value) as noise.

Even if the time resolution is not so extreme, in a case where the time resolution of the pupil diameter measurement device is relatively low (for example, measurement frequency=40 Hz or the like), in order for the estimation device 10 to smooth the pupil diameter data with the time window of 50 ms (time window of 50 points in length), smoothing is performed at only two data points. Therefore, it is considered that the variation amount of "data smoothed by a small time window" is greatly affected by noise and lacks reliability. Accordingly, also in such a case, it is considered that the estimation device 10 preferably applies the method B to the calculation of the micro variation amount of the pupil diameter rather than the method A.

When calculating the micro variation amount of the pupil diameter, the estimation device 10 may calculate both the value calculated by the method A and the value calculated by the method B, and may set an average value of these values or an average value of values weighted by these values as the micro variation amount of the pupil diameter.

[System Configuration and Others] Each component of each unit illustrated in the drawings is functionally conceptual and does not necessarily need to be physically configured as illustrated in the drawings. That is, a specific form of distribution and integration of individual devices is not limited to the illustrated form, and all or part thereof can be functionally or physically distributed and integrated in any unit according to various loads, usage conditions, and the like. Further, all or any part of each processing function performed in each device can be implemented by a CPU and a program executed by the CPU or can be implemented as hardware by wired logic.

In the processing described in the above embodiment, all or part of processing described as being automatically performed may be manually performed, or all or part of processing described as being manually performed may be automatically performed by a known method. In addition, the processing procedure, control procedure, specific names, and information including various pieces of data and parameters in the above description or the drawings can be arbitrarily changed, unless otherwise specified.

[Program] The estimation device 10 can be implemented by installing a program in a desired computer as package or online software. For example, by causing an information processing device to perform the determination program, the information processing device can be caused to function as the estimation device 10. The information processing device mentioned here includes a desktop or notebook personal computer. In addition, the information processing device also includes mobile communication terminals such as a smartphone, a mobile phone, and a personal handy-phone system (PHS) and terminals such as a personal digital assistant (PDA).

In addition, in a case where a terminal device used by a user is implemented as a client, the estimation device 10 can also be implemented as a server device that provides a service related to the processing described above to the client. In this case, the server device may be implemented as a web server or may be implemented as a cloud that provides a service regarding the above processing by outsourcing.

FIG. 5 is a diagram illustrating an example of the computer that executes an estimation program. A computer 1000 includes, for example, a memory 1010 and a CPU 1020. The computer 1000 further includes a hard disk drive interface 1030, a disk drive interface 1040, a serial port interface 1050, a video adapter 1060, and a network interface 1070. These units are connected to each other by a bus 1080.

The memory 1010 includes a read only memory (ROM) 1011 and a random access memory (RAM) 1012. The ROM 1011 stores, for example, a boot program such as a basic input output system (BIOS). The hard disk drive interface 1030 is connected to a hard disk drive 1090. The disk drive interface 1040 is, connected to a disk drive 1100. For example, a removable storage medium such as a magnetic disk or an optical disk is inserted into the disk drive 1100.

The serial port interface 1050 is connected to, for example, a mouse 1110 and a keyboard 1120. The video adapter 1060 is connected to, for example, a display 1130.

The hard disk drive 1090 stores, for example, an OS 1091, an application program 1092, a program module 1093, and program data 1094. That is, a program that defines each processing executed by the estimation device 10 is implemented as the program module 1093 in which a code executable by the computer is written. The program module 1093 is stored in, for example, the hard disk drive 1090. For example, the program module 1093 for executing processing similar to the functional configurations in the estimation device 10 is stored in the hard disk drive 1090. Note that the hard disk drive 1090 may be replaced with a solid state drive (SSD).

Data used in the processing of the above embodiments is stored in, for example, the memory 1010 or the hard disk drive 1090 as the program data 1094. Then, the CPU 1020 reads the program module 1093 and the program data 1094 stored in the memory 1010 and the hard disk drive 1090 to the RAM 1012 as necessary and executes the program module and the program data.

Note that the program module 1093 and the program data 1094 are not limited to being stored in the hard disk drive 1090 and may be stored in, for example, a removable storage medium and read by the CPU 1020 via the disk drive 1100 or the like. Alternatively, the program module 1093 and the program data 1094 may be stored in another computer connected via a network (local area network (LAN), wide area network (WAN), or the like). Then, the program module 1093 and the program data 1094 may be read by the CPU 1020 from another computer via the network interface 1070.

REFERENCE SIGNS LIST

10 Estimation device
11 Input/output unit
12 Storage unit
13 Control unit
131 Data acquisition unit
132 First smoothing processing unit
133 Second smoothing processing unit
134 Calculation unit
135 Estimation unit

The invention claimed is:
1. An estimation device comprising:
processing circuitry configured to:
  acquire time-series data of a pupil diameter during work of a subject of work performance estimation;
  smooth the time-series data of the pupil diameter of the subject by a first time window;

smooth the time-series data of the pupil diameter by a second time window that is a time window larger than the first time window;

calculate a difference between time-series data of the pupil diameter smoothed by the first time window and time-series data of the pupil diameter smoothed by the second time window; and estimate a level of work performance of the subject based on a magnitude of the difference between the time-series data of the pupil diameter smoothed by the first time window and the time-series data of the pupil diameter smoothed by the second time window, and output a result of the estimation.

2. The estimation device according to claim 1, wherein the processing circuitry is further configured to estimate that the larger the difference between the time-series data of the pupil diameter smoothed by the first time window and the time-series data of the pupil diameter smoothed by the second time window, the lower the work performance of the subject.

3. The estimation device according to claim 1, wherein the processing circuitry is further configured to estimate that the smaller the difference between the time-series data of the pupil diameter smoothed by the first time window and the time-series data of the pupil diameter smoothed by the second time window, the higher the work performance of the subject.

4. The estimation device according to claim 1, wherein the pupil diameter during work of the subject is a pupil diameter measured by an infrared camera or a visible light camera.

5. The estimation device according to claim 1, wherein the processing circuitry is further configured to calculates a first value that is an average value of absolute values of values obtained by first differentiating the time-series data of the pupil diameter smoothed by the first time window, calculate a second value that is an average value of absolute values of values obtained by first differentiating the time-series data of the pupil diameter smoothed by the second time window, and set an absolute value of a difference between the first value and the second value as the difference.

6. The estimation device according to claim 1, wherein the processing circuitry is further configured to set an average value of absolute values of differences between the time-series data of the pupil diameter smoothed by the first time window and the time-series data of the pupil diameter smoothed by the second time window at each time as the difference.

7. The estimation device according to claim 1, wherein the processing circuitry is further configured to exclude, from the time-series data of the pupil diameter, time-series data of the pupil diameter in a period in which a value of the pupil diameter is equal to or less than a predetermined threshold.

8. An estimation method performed by an estimation device, the estimation method comprising:

acquiring time-series data of a pupil diameter during work of a subject of work performance estimation;

smoothing the time-series data of the pupil diameter of the subject by a first time window;

smoothing the time-series data of the pupil diameter by a second time window that is a time window larger than the first time window;

calculating a difference between time-series data of the pupil diameter smoothed by the first time window and time-series data of the pupil diameter smoothed by the second time window; and estimating a level of work performance of the subject based on a magnitude of the difference between the time-series data of the pupil diameter smoothed by the first time window and the time-series data of the pupil diameter smoothed by the second time window, and outputs a result of the estimation.

9. A non-transitory computer-readable recording medium storing therein an estimation program that causes a computer to execute a process comprising:

acquiring time-series data of a pupil diameter during work of a subject of work performance estimation;

smoothing the time-series data of the pupil diameter of the subject by a first time window;

smoothing the time-series data of the pupil diameter by a second time window that is a time window larger than the first time window;

calculating a difference between time-series data of the pupil diameter smoothed by the first time window and time-series data of the pupil diameter smoothed by the second time window; and estimating a level of work performance of the subject based on a magnitude of the difference between the time-series data of the pupil diameter smoothed by the first time window and the time-series data of the pupil diameter smoothed by the second time window, and outputs a result of the estimation.

* * * * *